United States Patent [19]

Lannuzel

[11] Patent Number: 4,680,739
[45] Date of Patent: Jul. 14, 1987

[54] PROCESS FOR REMOVING ALL AMBIGUITY FROM THE MEASUREMENT BY DOPPLER EFFECT OF THE SPEED OF A MOVING TARGET

[75] Inventor: Olivier Lannuzel, Meaux, France

[73] Assignee: CGR Ultrasonic, Paris, France

[21] Appl. No.: 719,702

[22] Filed: Apr. 4, 1985

[30] Foreign Application Priority Data

Apr. 6, 1984 [FR] France .................................. 84 05485

[51] Int. Cl.$^4$ .......................... G01S 9/66; A61B 5/02; G01F 1/708
[52] U.S. Cl. ...................................... 367/90; 367/91; 128/663; 73/861.05
[58] Field of Search ..................... 367/90, 91; 128/663; 73/861.06, 861.25; 343/8; 356/28.5; 342/104, 105

[56] References Cited

U.S. PATENT DOCUMENTS

| | | | |
|---|---|---|---|
| 3,617,995 | 11/1971 | Goulet | 367/91 |
| 3,762,221 | 10/1973 | Coulthard | 128/663 X |
| 4,067,236 | 1/1978 | Hottinger | 128/663 X |
| 4,485,821 | 12/1984 | Iinuma | 128/663 |
| 4,573,477 | 3/1986 | Namekawa et al. | 128/663 |
| 4,583,409 | 4/1986 | Lannuzel et al. | 73/861.25 |

FOREIGN PATENT DOCUMENTS 0073418 8/1982 European Pat. Off. .
0092841 4/1983 European Pat. Off. .

OTHER PUBLICATIONS

Sainz, A.; Roberts, V. C.; A New Approach to Doppler Ultrasound Flowmetry; Ultrasonics International Conference 1977.
1973 Ultrasonics Symposium Proceedings, Monterey, Calif., 507 Nov. 1973, Institute of Electrical and Electronics Engineers, . . . .
Elektronik, vol. 26, No. 4, 1977, Munich (DE); A Marganitz: "Mikrowellen-Tachometer misst beruhrunglos . . .".

Primary Examiner—Thomas H. Tarcza
Assistant Examiner—Tod Swann
Attorney, Agent, or Firm—Roland Plottel

[57] ABSTRACT

The present invention concerns a process for removing all ambiguity from the measurement by the Doppler effect of the speed of a target. It consists in obtaining a signal of Doppler shift relating to a series of ultrasonic pulses sent in the direction of the target and received after their reflection onto this target, the recurrence frequency of the pulses constituting an ambiguity limit of these speed measurements, wherein the measured Doppler shift is transposed by modulating the signal received by a signal at a frequency called determination frequency, so as to bring from a known value the spectral components to be analyzed in the useful measuring band and after measuring the true speed values are worked out by adjunction of a correction that depends upon the determination frequency that is used, this process being applicable to measuring the speed of blood in the medical field.

13 Claims, 9 Drawing Figures

FIG_1

FIG_4

FIG_5

FIG_6

FIG_7

FIG_8

PROCESS FOR REMOVING ALL AMBIGUITY FROM THE MEASUREMENT BY DOPPLER EFFECT OF THE SPEED OF A MOVING TARGET

BACKGROUND OF THE INVENTION

1. Field of the Invention

The present invention concerns a process for removing all ambiguity from measurements by the Doppler effect of the speed of a target. The term "target" to which reference is made in this invention must be construed in its widest meaning; in particular, it can be a fluid flowing into a tube. This invention can have an excellent application in the medical field; the fluid in this case is the blood flowing in an artery or in a vein and the target is thus an elementary volume of this blood in a specific site of the human body, for example, close to the heart. The problems that are raised by measuring the speed of a moving target are set out and overcome herein-below in such an application of the medical type.

2. Description of the Prior Art

When the speed of a moving target is measuring by the Doppler effect by utilizing ultrasound techniques, a sonic or acoustical pulse of a relatively brief duration is emitted in the direction of this target. This pulse is propagated from an emitting probe through the environment that surrounds the target and is reflected onto this target in a sonic or acoustical pulse. It is retrodiffused in all directions and in particular in the direction of a remote sensing element or measuring pick-up. The sensors utilized are generally of a reversible type which means that a single sensor can emit the sonic or acoustical pulse and subsequently receive the reflected pulse. If the emitted pulse vibrates at a frequency $f_o$ the reflected pulse vibrates at a frequency that is shifted relatively to $f_o$ by the Doppler effect. The amplitude of this shift measures the radial component of the target speed along the outward-inward axis of propagation of these pulses. Since there is not only the target which reflects the pulse, it is known to open a receiving time window at the end of a determined duration following the beginning of the pulse emission, to receive the reflected sonic or acoustical vibration which corresponds to the target and only to the target. This determined duration corresponds to the ratio of the distance separating the target and the sensor at the speed of propagation of the pulses in the environment that surrounds the target.

Indeed, instead of emitting a single pulse and receiving a single pulse, sonic or acoustical pulses are periodically emitted and reflected pulses are periodically received. This emitting periodicity is dependant, on the one hand, upon the will of the user to know the speed of the blood flow in different places of a studied organ; in this case, the receiving window is displaced in time from one measurement to the other. On the other hand, since all the particles of an elementary volume of a fluid are not displaced at the same speed, it is thus necessary to calculate the mean speed of the elementary volume at one place involved and thus to carry out the spectral analysis of the reflected pulse which in the present state of the art cannot be carried out by receiving a single pulse but can only be carried out by combining the measurement of several successive reflected pulses.

The immediate consequence of this periodicity is to limit the admissible Doppler effect which can be directly measured. In fact, operating proceeds in the same way as if the phenomen studied, i.e. the blood in movement, was subjected to a stroboscopic illumination. The elementary volumes, the speed of which provokes a Doppler shift substantially equal to the recurrence frequency, are seen substantially as not moving. The elementary volumes which are displaced slightly more rapidly than a nominal speed for which the Doppler shift is equal to the half recurrence frequency, are even interpreted as being displaced in counter direction to their true displacement. The phenomenon is reproduced, of course, for every Doppler shift that is a whole multiple of the half recurrence frequency. If the user does not have access to the true speed, he only has access to the measured speed: this means that for this user there is always an ambiguity. This ambiguity raises the question as what is the true speed of the elementary volume studied while being aware of the measured value obtained.

Two types of solutions are known in the prior art that attempt to overcome this problem. The first solution consists in increasing the recurrence frequency $F_r$ so as to bring as high as possible the ambiguity threshold. If we call the measurement of the Doppler shift corresponding to a given speed $f_m$, the nominal speed, i.e. that which can be admissibly measured, is such that $f_m = F_r/2$. Consequently, the more the recurrence frequency increases, the further the ambiguity threshold is pushed towards high values: if possible beyond the range of speeds that it is desired to measure. The first technique has two drawbacks. The first drawback is on the physiological level since the more the recurrence frequency increases, the higher the number of pulses sent into the patients body. It is questionable whether at high doses the ultrasonic excitations do not destroy certain cells of the human body. The second drawback is that the fact of increasing the recurrence frequency correlatively diminishes the period that separates two successive excitation pulses. This limits the time adjustment range of the position of the time receiving slot or window. In other words, it is the exploration depth from the sensor which is reduced.

In certain cases there can even be measuring errors linked to the fact that during the time receiving slot a signal is received that corresponds to the reception of an emitted pulse which is reflected at a given depth of the studied environment and which also corresponds to the reception of a preceding pulse but reflected in a deeper zone of this environment. In other words, if the exploration depth obstacle can be overcome, it remains that the measuring result takes simultaneously into account the interference of the deeper parts which falsifies said measurement. In a practical example, if frequency $f_o$ is equal to 7 MHz and if the radial component of the speed of the blood is about 3 m/s, in the human body, the speed of propagation is about 1500 m/s, the corresponding Doppler shift is about 30 KHz and the maximal exploration depth is about 2.5 cm. Thus, the radial speed of 3 m/s is representative of a blood flow speed of about 5 m/s if the axis of propagation of the pulses is oriented substantially at 60° with respect to the means direction of the blood at the place of measurement (which corresponds to a general experimentation mode). Since the patients to be examined are frequently patients suffering from heart trouble, the true speed of the blood can be exceedingly higher (due to the fact, especially of aortic stenosis). Therefore, even in the case where the recurrence frequency is high and where the exploration depth is reduced, measurement ambiguities are possibly encountered.

A second technical solution consists in causing to drop the frequency of the sonic or acoustical signal emitted. If $f_o$ is this sonic or acoustical frequency, the Doppler shift $f_d$ can be expressed in the form of $$f_d = 2.v f_o / c$$

in which v is the speed to be measured and c is the speed of propagation of the sonic or acoustical pulse in the environment. For a given speed v, $f_d$ will be that much weaker as $f_o$ is itself low. The drawback of this choice is that there is a important loss of sensitivity on the determination of $f_d$.

The object of the present invention is to overcome the drawbacks cited herein-above by proposing a process in which the signal representing the Doppler shift to be measured is modulated by a signal at a known frequency. The effect of this is to tranpose in the field of the frequencies the ambiguity thresholds and to allow the elaborate a measurement called a shifted measurement of the true value. The true value is found by correcting the shifted value of a value corresponding to the modulating frequency introduced.

The object of the invention is a process for removing all ambiguity from the measurement by Doppler effect of the speed of a target in which:

- a pulse vibrating at a sonic or acoustical frequency is emitted in the direction of the target, periodically at a recurrence frequency;
- the ultrasonic pulse retrodiffused by the target is received;
- a complex demodulation of the signal received is carried out, by a signal of the same frequency as the emitting sonic or acoustical frequency;
- the speed of the target is computed by spectral analysis from the measurement of the Doppler shift signal resulting from this demodulation,—this shift being representative of the speed of the target—, the determination ambiguity of the speed of the target being induced by the importance of this shift with respect to the half recurrence frequency;
- the said demodulated signal is modulated by a signal oscillating at a frequency called determination frequency so as to transpose, from a known value, the Doppler shift to be measured in a band smaller than the half recurrence frequency;
- and in that the computing of the speed of the target consists in calculating by spectral analysis a speed called shifted speed from this modulated signal and in correcting the said shifted speed by a value corresponding to the determination frequency in order to elaborate the true value of the speed to be measured.

BRIEF DESCRIPTION OF THE DRAWING

The invention will become more apparent by reading through the following description and by examining the figures appended thereto. This description is given by way of non-limitative illustration. In the figures, the same references designate the same elements. They represent.

DESCRIPTION OF THE PREFERRED EMBODIMENTS

Figure 1:
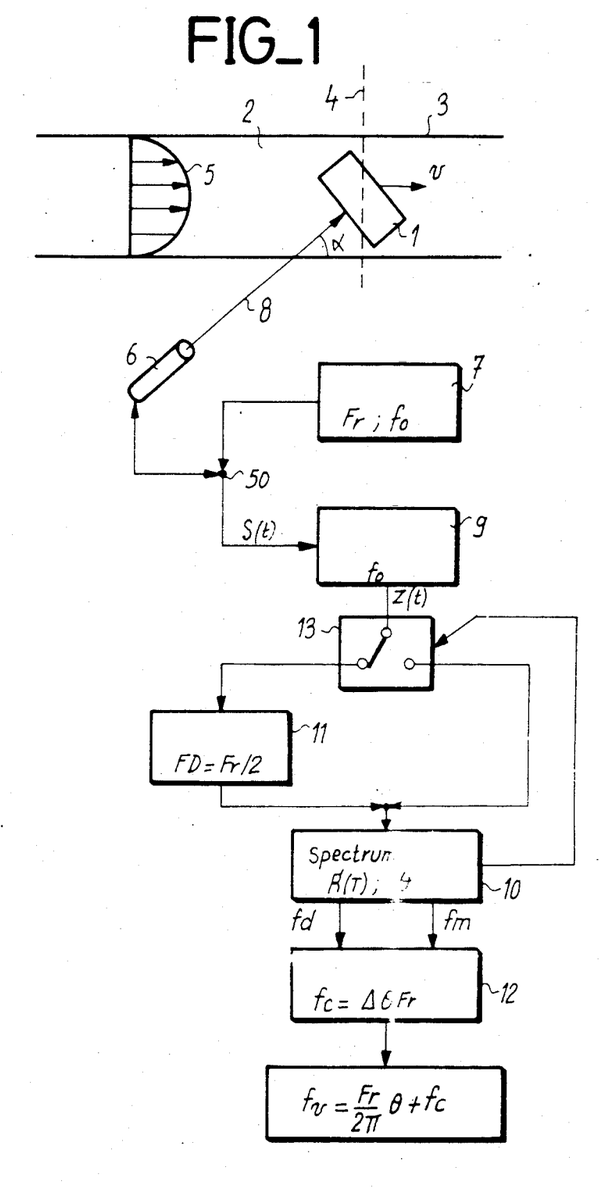
FIG. 1 a schematic representation of a device carrying out the process according to the invention.

FIG. 1 represents the outline of a device for carrying out the process according to the invention. It allows to measure the mean speed of an elementary volume 1 of a fluid 2 circulating in a tube 3. Elementary volume 1, which is a target in the widest meaning of the word, is a group of particles of fluid 2 which are present in a particular place of tube 3: section 4. Fluid 2 having a speed diagram symbolically represented in 5 is displaced at a certain average speed v that it is desired to measure. In order to do this, a series of sonic or acoustical pulses are emitted by means of a sensor 6 of the piezoelectric type and of a generator 7. These sonic or acoustical pulses vibrate at a sonic or acoustical frequency $f_o$ and are emitted periodically as a recurrence frequency $F_r$. The inward-outward axis of propagation 8 of the sonic or acoustical waves between volume 1 and sensor 6 forms an angle alpha with the mean flow direction of fluid 2. Each pulse that insonifies volume 1 is retrodiffused in the direction of sensor 6 by vibrating about frequency $f_o$, being shifted from this frequency by a value proportional to the flow speed and to the cosine of angle alpha. This being such, the influence of angle alpha will be disregarded in the following description.

Sensor 6 is of the reversible type; i.e. the piezoelectric crystal that it comprises delivers a sonic or acoustical pulse when it is subjected to an electric signal at the moment of the emission, and delivers an electric signal when it is subjected to a sonic or acoustical excitation at the moment of receiving. Outside the emitting time, the sonic or acoustical signal received is transmitted towards a receiver 9 by any known means, in particular through a duplexer 50. In the receiver 9 the signal received is time filtered amnd is demodulated by a signal at frequency $f_o$. The result of this demodulation is to cause to appear a representative signal of the Doppler shifts only at the site of section 4.

In known processes according to the prior art, the spectral analysis of this Doppler shift is carried out in a spectrum analyser device 10. When this Doppler shift is greater than half the sampling frequency, a folding over of the signal of this Doppler creep occurs which is incorrectly interpreted by circuit 10. One feature of the present invention is that the signal introduced into analysis circuit 10 is not the signal demodulated by receiver 9 but rather this demodulated signal having undergone a modulation in a modulator 11 by a signal at a frequency called determination frequency FD. This modulation consists in transposing towards the lower frequencies by a value FD, the spectrum of the signal of the Doppler shift. With a suitable filtering, it is possible to recover this transposed spectrum alone. Frequency FD being known, it is thus possible to affect the result $f_d$ delivered by analyser 10 by a known correction $f_c$ in a correction circuit 12.

Since there is a biunivocal correspondence between the speed v of the target 1 and the value of the true corresponding Doppler shift, reference will only be made in the remainder of the description to the frequencies of these Doppler shifts. Therefore, the true frequency $f_v$ is the sum of the frequency called shift frequency $f_d$ delivered by analysis circuit 10 and correction frequency $f_c$ delivered by circuit 12. The measured frequency $f_m$ corresponds to that delivered by analyser 10 when modulator 11 is not caused to intervene. It will be seen from the following description that the invention allows to interpose or not modulator 11 according to whether the Doppler shift to be measured is situated in a range with or without ambiguity. Symbolically, a commutator 13 the position of which depends upon the value measured by analyser 10 allows to interpose or to shunt this modulator 11 between receiver 9 and analyser 10.

Figure 2:
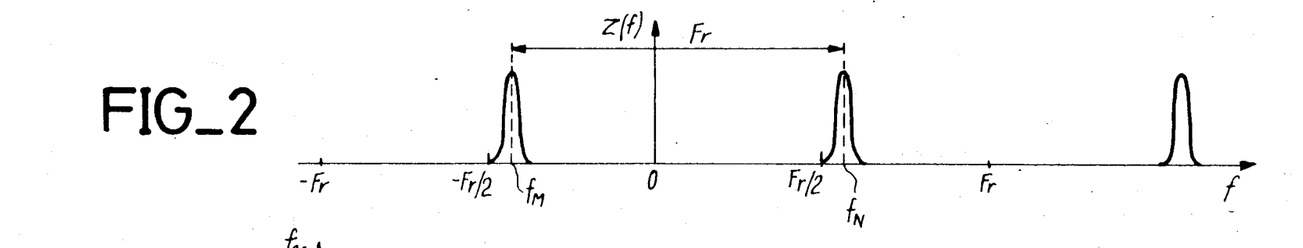
FIG. 2 the diagram of the frequency spectrum of a signal to be analyzed by the process according to the invention.

FIG. 2 represents the diagram Z(f) of the Doppler spectrum of the signal Z(t) delivered after demodulation in receiver 9. The periodic insonification of target 1 consists in sampling Z(t) since Z(t) is withdrawn at each period. Due to this sampling at frequency $F_r$, the spectrum of Z(t) has a periodicity of $F_r$. FIG. 2 represents a spectrum of Z(f) that does not have a monfrequency. It extends slightly on either side of a mean frequency $F_M$ and thus indicates that all the parts of target 1 are not displaced at the same speed, but are each displaced at speeds close to the mean speed. The diagram of FIG. 2 again indicates that it is the frequency $f_M$ which will be analyzed in analyser 10, without it being possible to know whether $f_M$ is the true frequency or an ambiguous frequency $f_N$, shifted from $f_M$ by a whole multiple of the sampling frequency.

Figure 3A:
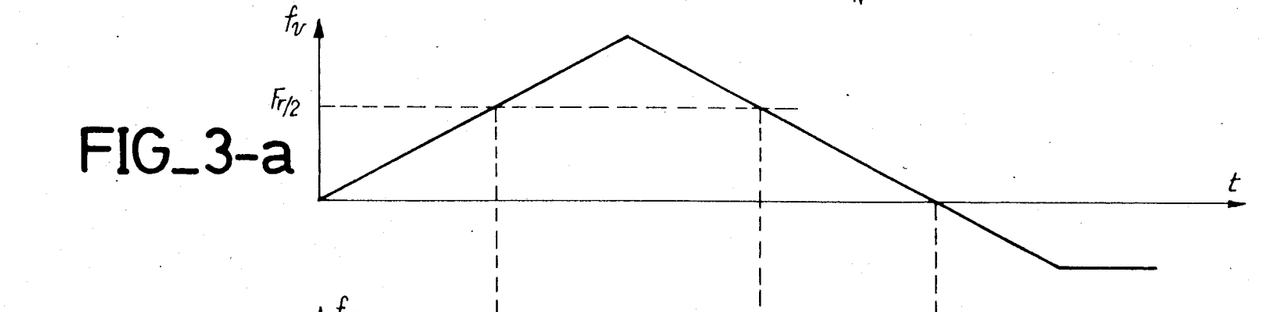
FIGS. 3a and 3b time diagrams of the time variations of the speeds of a target and of the corresponding signals measured intervening in the process according to the invention.
Figure 3B:
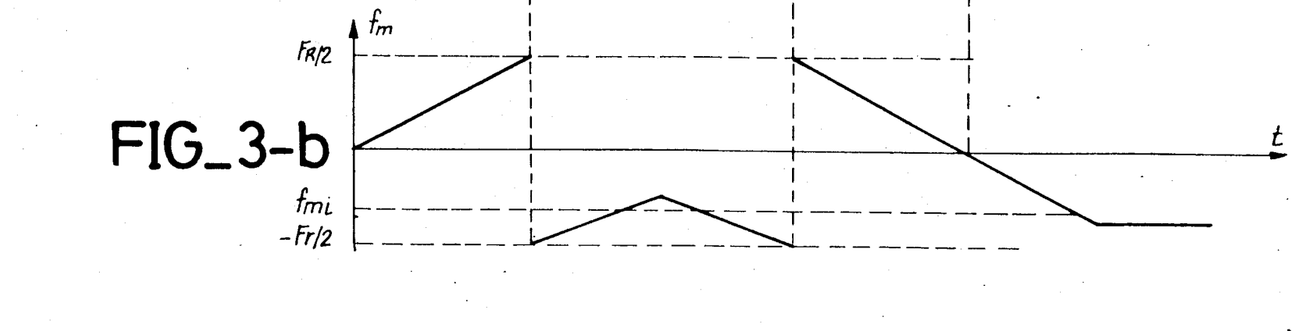

FIGS. 3a and 3b represent respectively and in correspondance with time the changes of the true frequency $f_v$ and of the measured frequency $f_m$. In one example, at a frequency $f_{mi}$ the measurement corresponds to a negative speed whereas in fact the speed is simply higher than the nominal speed that can be measured by analyser 10. Furthermore, the signification ambiguity of the measurement $f_{mi}$ is revealed since this measured frequency corresponds to two possible values different from the flow speed.

Figure 4:
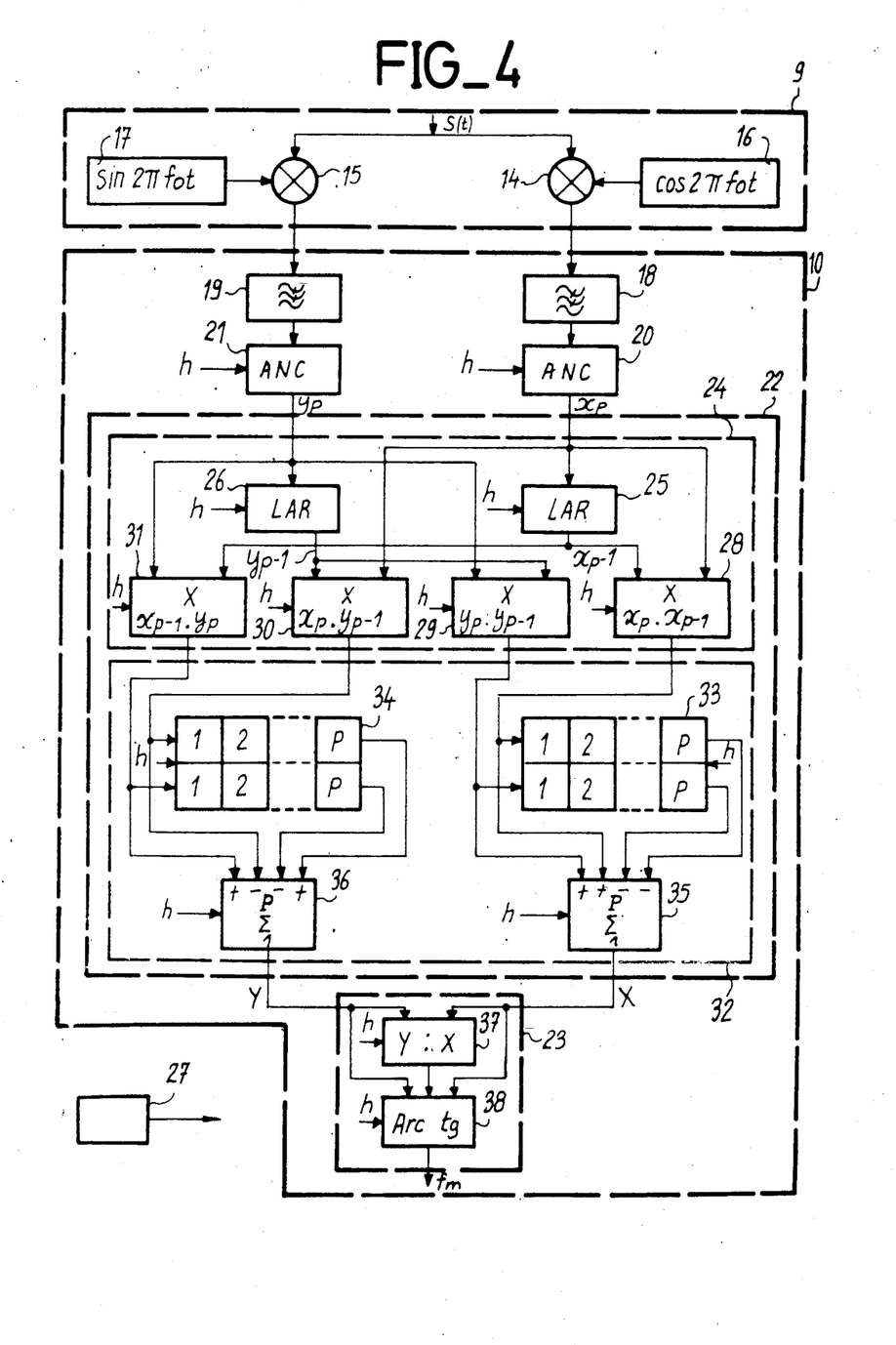
FIG. 4 an outline of a spectral analysis circuit particularly adapted for carrying out the process according to the present invention.

FIG. 4 represents a spectrum analysis device carrying out a process for calculating the mean speed of elementary volume 1 of a fluid. This process is based on the fact that the mean flow speed of an elementary volume of a fluid corresponds at the moment of order one of the Fourier transform of the Doppler shift provoked by this elementary volume, and the fact that this moment of order one of the Fourier transform is equal to the order one derivate of the self-correlation function R(t) of the time signal of the Doppler shift. Outside the reconstitution in shape and return to scale to which are subjected signal S(t) transmitted by sensor 6 to receiver 9, this receiver comprises two demodulators 14 and 15 each receiving the signal S(t) on their first input. On their second input they receive respectively the signals in quadrature, cos $2\pi f_o t$ and sin $2\pi f_o t$ delivered by two oscillators in quadrature 16 and 17. These two demodulators carry out a transposition of the Doppler spectrum of a width equal to $f_o$. They carry out a demodulation called a demodulation in quadrature since the signals that impair them on their second input are in quadrature phase with respect to one another.

Each of the demodulated signals is made to pass through a low-pass filter respectively 18 and 19 in analyser 10, and they are quantified in samplers respectively 20 and 21, each comprising a sampler-blocker followed by an analog-numerical converter (CAN). A complex sampled signal is thus obtained, the real part $x_p$ of which is delivered by the sampler 20 and the imaginary part $y_p$ of which is delivered by sampler 21. Therefore, at each recurrence sample of the signal Z(t) a quantified sample $z_p = x_p + jy_p$ is withdrawn. Spectral analysis circuit 10 comprises further a circuit 22 to calculate the self-correlation function R(T) of the signal Z(t) and a circuit 23 to calculate the order one derivate of this self-correlation function. Since signal Z(t) is sampled and complex, the self-correlation function becomes discrete, r(T) and complex. The real part of r(T) is X, its imaginary part being Y.

The result elaborated in the process evoked allows to write that the mean frequency $f_m$ measured by such a spectral analysis device is given by the following formula:

$$f_m = \frac{F_r}{2\pi} Arg \{r(T)\} \text{ with } T = \frac{1}{F_r}$$

It is then necessary to calculate the argument of this discrete self-correlation function $r(1/F_r)$. Then, $r(1/F_r)$ can be expressed as:

$$r\left(\frac{1}{F_r}\right) = Z = X + jY = \overset{P}{\Sigma} ((x_p + jy_p)^*(x_{p-1} + jy_{p-1})) = \overset{P}{\Sigma} (z_p^* \cdot z_{p-1})$$

In this expression, p is the time index of a sample of the demodulated signal delivered by analog-numerical converters 20 and 21 p-1 is the rank of the sample that appears immediately prior to the sample of rank p. The number P corresponds to a precision optimum of the measurement. In one example, P is equal to about a hundred. The exponent * indicates the complex conjugation.

In other words, knowledge of a certain number of samples $z_n$ allows to calculate the self-correlation function of the signal S(t) being demodulated as well as its order one derivate. This is expressed by the capital Sigmas that are present at the end of the expression cited herein-above. Thus, the argument $\theta$ of a complex number Z (representative of the self-correlation function) is equal, within certain limitations, to the arc-tangent of the ratio of its imaginary part to its real part. This can be written as $$\theta = Arg(Z) = Arctg(Y/X)$$

This equality is only true in the field of the definition without discontinuity of the arc-tangent, i.e. between $-(\pi/2)$ and $+(\pi/2)$. If the argument of Z is comprised between $-\pi$ and $-(\pi/2)$ it is necessary to withdraw the value $\pi$ from the calculation made by means of the arc-tangent; if the argument of Z is comprised between $+(\pi/2)$ and $+\pi$ it is necessary to add $\pi$. The indetermination on $\theta$ is thus suppressed. This being expressed, it will now be explained how analyser 10 calculates in real time the self-correlation function Z as well as its argument $\theta = \text{Arg}(Z)$. In a second time, it will be shown what is the incidence on the calculation of the modulation of S(t) by a very precise determination frequency FD which is equal to half the recurrence frequency. It will furthermore be explained in the framework of this calculation the great interest involved by making this particular choice. By reverting to the formula allowing to calculate the self-correlation function in function of the values of the complex samples $z_p = x_p + jy_p$ the following can be written:

$$X = \overset{P}{\Sigma} (x_p \cdot x_{p-1} + y_p \cdot y_{p-1}) \text{ and } Y = \overset{P}{\Sigma} (y_p \cdot x_{p-1} - y_{p-1} \cdot x_p)$$

Circuit 22 comprises delay means 24 in order to know, at every pulse received the values $x_p$ and $y_p$ of the sampled complex signal corresponding to the sample of rank p and to know the same elements of the immediately preceding sample, i.e. rank p-1. Delay means 24 comprise two delay lines, respectively 25 and 26 connected in series to the outputs of samplers 20 and 21. These delay lines 25 and 26 only deliver at their outputs the information data that they receive at the instant t at the end of a time period t+T, where T corresponds to the above-mentioned recurrence period. In practice, these delay lines can be constituted by shift registers receiving at their parallel inputs the binary data of the quantified signal delivered by the samplers, and restituting these data on their outputs in parallel under the effect of a clock pulse h elaborated by a sequencer 27. This sequencer 27 is synchronized with the emission of the pulses; the sampling frequency is thus equal to the recurrence frequency since converters 20 and 21 are also controlled by signal h.

Delay means 24 comprise furthermore a set of multipliers 28 to 31 receiving at their inputs the real parts x or imaginary parts y of the sampled complex signal; corresponding to a given sample and a preceding sample, to carry out, at a rhythm dictated by sequencer 27, respectively the following multiplications:

$$x_p \cdot x_{p-1}, \ y_p \cdot y_{p-1}, \ x_p \cdot y_{p-1}, \ x_{p-1} \cdot y_p$$

Circuit 22 comprises, in cascade with delay means 24, summator-accumulator means 32 comprising a set of two shift registers 33 and 34 connected respectively to two summators-accumulators 35 and 36. These shift registers each contain 2P.cases (P corresponds to the optimum number of samples). These registers receive the products elaborated by multipliers 28 and 29, on the one hand, and 30 and 31, on the other hand. At each impulse of sequencer 27, a couple of real products ($x_p \cdot x_{p-1}$ and $y_p \cdot y_{p-1}$) and a couple of imaginary products ($x_p \cdot y_{p-1}$ and $x_{p-1} \cdot y_p$) are introduced respectively into the shift registers, while a couple of real or imaginary corresponding products but from the lower rank (from rank p-P; $x_{p-P} \cdot x_{p-1-P}$, $y_{p-P} \cdot y_{p-1-P}$, and $x_{p-P} \cdot y_{p-1-P}$, $x_{p-1-P} \cdot y_{p-P}$) are extracted from these registers. Summators-accumulators 35 and 36 thus add the products introduced at the same time as they subtract the extracted products. Once the first samples P have been acquired, firstly each of the shift registers receives in introduction a product corresponding to the rank of the following sample and secondly delivers in extraction the products corresponding to the ranks lower than P. In the summators-accumulators 35 and 36 the products introduced and extracted are admitted at inputs affected by a particular sign according to which it is necessary to add or to subtract these products.

In the case of summator-accumulator 35, which delivers the real part X of the self-correlation function, all the new products introduced into the registers are affected with sign + whereas all the old products extracted are affected with a sign −. This means that summator-accumulator 35 permanently contains, thus in real time, the real part of the self-correlation function which would have been concerned the samples P that precede the instant at which the contents of this summator-accumulator 35 are withdrawn. A similar reasoning can be made for summator-accumulator 36 by noting, however, that it is specialized in the calculation of the imaginary part of the self-correlation function in which Sigma comprises a subtraction of the products. All the circuits of means 32 are controlled by sequencer 27. Taking into account a sampling frequency of about ten KHz, calculating time for these circuits is about 100 microseconds. In the present state of the art, the calculating speeds of integral circuits are such that these operations do not present any difficulty. In practice, these circuits can be replaced by a microprocessor, the general algorithm of which reproduces that which has been described immediately herein-above.

In particular, this microprocessor can furthermore carry out the operation represented by circuit 23 for calculating the derivate of order one of the self-correlation function. In this circuit 23 a divider 37 realizes the ratio of the imaginary part Y to the real part X. An arc-tangent table 38 connected to divider 37 delivers the argument of the self-correlation function as a function of the ratio worked out by divider 37. In order to remove the indetermination linked to a calculation by the arc-tangent, table 38 also receives value X and value Y. Indeed, if the argument of Z is comprised between $-\pi$ and $-(\pi/2)$ this means that X is negative and Y is positive. If the argument is comprised between $+(\pi/2)$ and $\pi$ this means that X is negative and Y is positive. Consequently, table 38 receives in address, on the one hand, the value of X/Y ratio and, on the other hand, the information data concerning the sign of X and the sign of Y. It can carry out without indetermination the argument sought and more generally the calculation of value $f_m$.

For a given signal S(t) the result of its modulation by a signal at a determination frequency FD can be expressed in the following form:

$$(S(t) \text{ modulated}) = S(t) \cdot e^{-j2\pi FDt}$$

In the present case, since the singal S(t) is sampled at dates $t = p/F_r$, where $p/F_r = p.T$, this corresponds to a periodic sampling of period T. Thus, the expression of modulated and sampled S(t) becomes:

$$(S(t) \text{ sampled modulated}) = S(t) \cdot e^{-j2\pi \frac{FD}{F_r} \cdot p}$$

or again by expressing S(t) in its quantified form it becomes:

$$(S(pT) \text{ sampled modulated}) = z_p e^{-j2\pi \frac{FD}{F_r} \cdot p}$$

where $z_p = x_p + jy_p$.

At this stage of the description, it will be revealed that it is particularly useful to cause $FD=F_r/2$. Indeed, in this case the complex exponential case representative of the modulation becomes:

$$e^{-j2\pi \frac{F_r}{2F_r} P} = e^{-j\pi P} = (-1)^P$$

This particularly simple result allows to express that if signal S(t) is modulated, the quantified sample $z_p$ is replaced by $(-1)^P . z_p$. In other words, in the calculation of the self-correlation function given hereinabove:

$$r\left(\frac{1}{F_r}\right) = \sum^P z_p^* \cdot z_{p-1}$$

each sample $z_p$ must be multiplied by $+1$ or $-1$ according to whether the rank of p is even or odd. Indeed, it is even possible to suppress this operation which would consist in changing the sign, every other time, at the rhythm of their arrival, of the values $x_p$ and $y_p$ delivered by analog-numerical converters 20 and 21. In fact, it is worthwhile noting that:

$$(-1)^P . (-1)^{P-1} = -1$$

This simply means that the modulation of S(t) by a signal at a determination frequency equal to $F_r/2$ consists in changing the sign of the self-correlation function with respect to the value that it would have had if it had not been modulated. In other words, modulated Z equal $-Z$. This finding is interesting since it will be noted that finally the introduction of the modulation could occur subsequently, i.e. with knowledge of the value of Z (or its argument $\theta$ whichis equivalent). The shifting affecting $\theta$ due to the modulation must be compensated in order to relocate the true value. In the present case where $FD=F_r/2$; this correction is equal to $+\pi$. The question thus arises from what value it is appropriate to "modulate", since after every step the decision can be taken to modulate or not.

Figure 5:
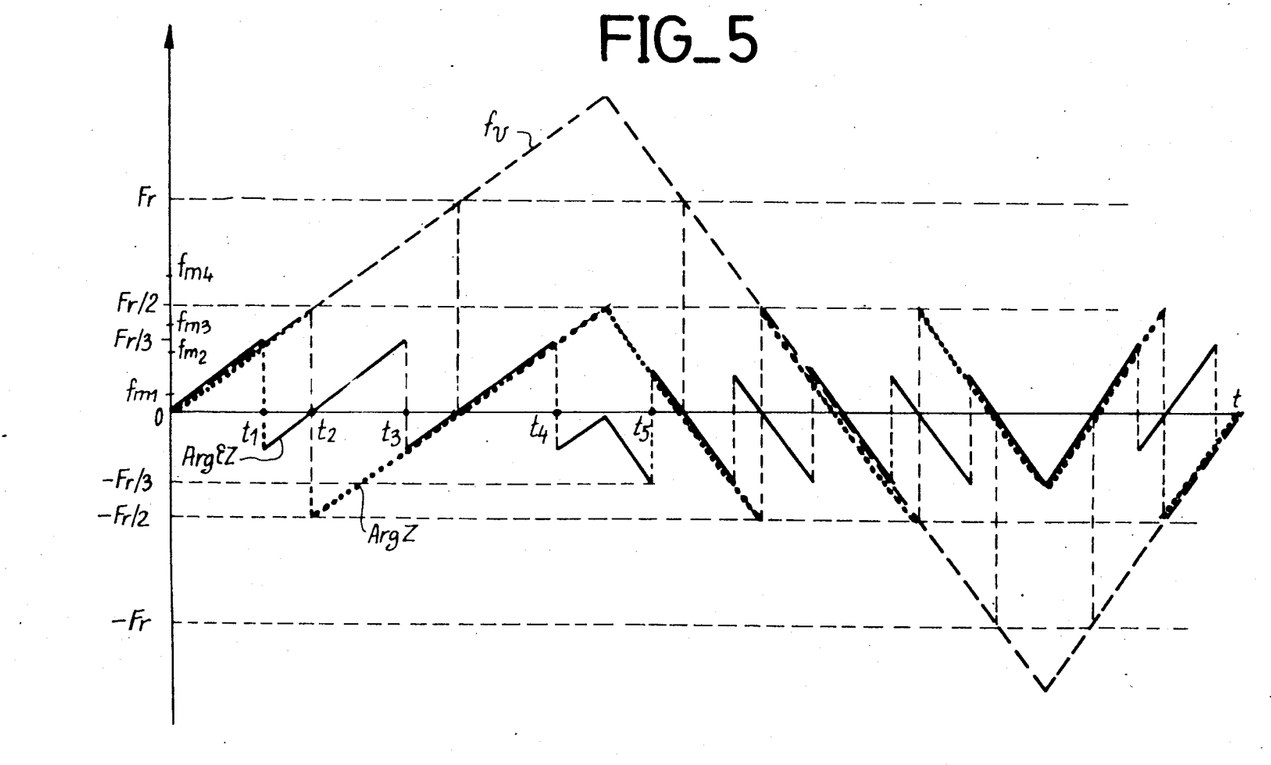
FIG. 5 a time diagram of the shifted speed and of the true speed.

FIG. 5 represents a phenomenon that corresponds to a target, or the elementary volume of a fluid, the value of the speed of which continuosly changes during time. This could represent the flow speed of the blood in the patient's heart. The description that follows as to this phenomenon is, of course, applicable to heart cases even if the speed of the blood flow there is generally oriented in a unique direction.

The diagram of FIG. 5 presents three graphs; the first graph drawn in dashed lines represents the true speed $f_v$ (all elements are expressed here in the form of the means Doppler shift, i.e. in frequential terms). It represents, in fact, the signal that it is sought to produce.

A second graph drawn in dotted lines is proportional to the variation of the argument of Z; it is the result $f_m$ that circuit 22 delivers when there is no modulation. This second graph presents the ambiguities that are encountered in FIG. 3b. The third graph drawn in a full line is proportional to $Arg(\epsilon Z)$ with $\epsilon = \pm 1$ according to modulation or no modulation has occured. When the dotted line is colinear to the full line, no modulation has occured; when the dotted line is not colinear to the full line, modulation has occured.

The processing to which $Arg(\epsilon Z)$ is subjected is a processing carried out by a microprocessor. The behaviour of this processing is more flexible here than in a cabled circuit. It is, however, possible to construct such a cabled circuit from the description of the processing algorithm described herein-below. The following convention bearing on the sign of $\epsilon$ is retained:

if $\epsilon = +1$, $\theta = Arg(Z) = Arctg \frac{Y}{X}$ if $\epsilon = -1$, $\theta = Arg(-Z) = Arctg \frac{Y}{X} - \pi$ if Y is positive or $\theta = Arg(-Z) = Arctg \frac{Y}{X} + \pi$ if Y is negative This convention allows to pass from the dotted line to the full line. In fact, the distinction bearing upon the sign of $\pi$ is equivalent to testing the sign of Y. The convention will become more apparent by examining in association FIGS. 5 and 7. This latter represents the theory calculation of an argument from a value of the arc-tangent. Therefore, for a first value of Doppler shift $f_{m1}$ comprised between zero and $F_R/4$, X and Y are positive and $\theta$ is equal to Arctg Y/X; $\epsilon$ being equal to 1, there is no modulation.

Figure 7:
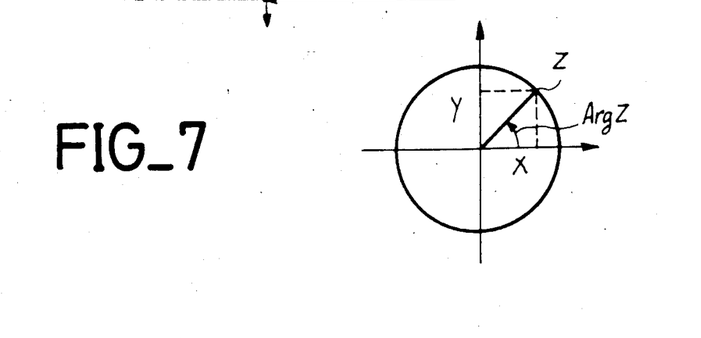
FIG. 7 a symbolic representation of the measurement of the Doppler shift.

For a second measured value $f_{m2}$ comprised between $F_R/4$ and a certain threshold value, here equal to $F_r/3$, Z is present in the upper left-hand frame of FIG. 7. In this case, $\theta$ is given again in the same conditions; there is no modulation. On the contrary, for a third measured value $f_{m3}$, higher than threshold $F_r/3$ but lower than $F_r/2$, modulation was carried out, thus the sign of $\epsilon$ was changed whereas Y was positive. It will indeed be noted that Y is positive up until $f_{m3}$ reaches $F_r/2$. The preceding convention is thus verified where in this case $\pi$ was subtracted from Arctg Y/X. For measurement $f_{m4}$, close to but higher than $F_r/2$; Y has become negative, the value of the argument of Z changing sign. The graph in a full line is thus obtained again from the dotted line by adding $\pi$ to Arctg Y/X. Consequently, in the invention $\theta$ is always calculated so that $\theta$ is equal to $Arg(\epsilon Z)$ according to the convention that has immediately been indicated herein-above to pass from the dotted line graph to the full line graph.

The choice of the threshold value, here $F_r/3$ from which it is decided to modulate is imposed by the following criteria; it is sought to obtain the widest possible variation range of the measured signal so that the evolution of the measurement around this value induces as few as possible permutations between the situations where there is modulation and the situations where there is no modulation. It is necessary to know in order to understood this criteria that this threshold is a threshold given in absolute value. This means that there is passage from one situation to the other once the value obtained, with or without modulation according to the case, negatively or positively exceeds this threshold value. The shift in frequence brought to the measurements $f_m$ is proportional to $\pm \pi$ and it is therefore equal to $\pm F_r/2$.

The choice of a threshold at $F_r/4$ brings after shift to transform $f_m$ close to $+F_r/4$ in $f_d$ close to $-F_r/4$. if the Doppler shift to be measured evolves above and below $F_r/4$, it will be constantly changing from one situation with modulation to another situation without modulation and vice versa. It is therefore of interest to remove this threshold as far as possible from $F_r/4$. If $F_r/2$ is chosen as the threshold, it is a maximum since, of course, Arg(Z) calculated by circuit 10 never exceeds that value. But another problem again occurs here. It this case, indeed, the variation range is maximum, which is favourable, but the intervention of the low-pass filters 18 and 19 has the effect of severely disturbing signal S(t) demodulated around these Doppler shift values. In fact these filters cut exactly at $F_r/2$ so as to scrupulously respect the conditions of a good sampling imposed by Shannon's theorem. Finally, this will mean passing from one demodulated situation to another non-modulated situation for threshold values that are not reached in a strict manner by the Doppler shift to be measured. Furthermore, is must be recalled that these Doppler shifts are not monofrequency Doppler shifts but are mean Doppler shifts calculated on relatively wide spread spectrum as represented in FIG. 2. A preferred threshold value is $F_r/3$. Another preferred value is $3F_r/8$. The explanation that follows is given for $F_r/3$.

Figure 6:
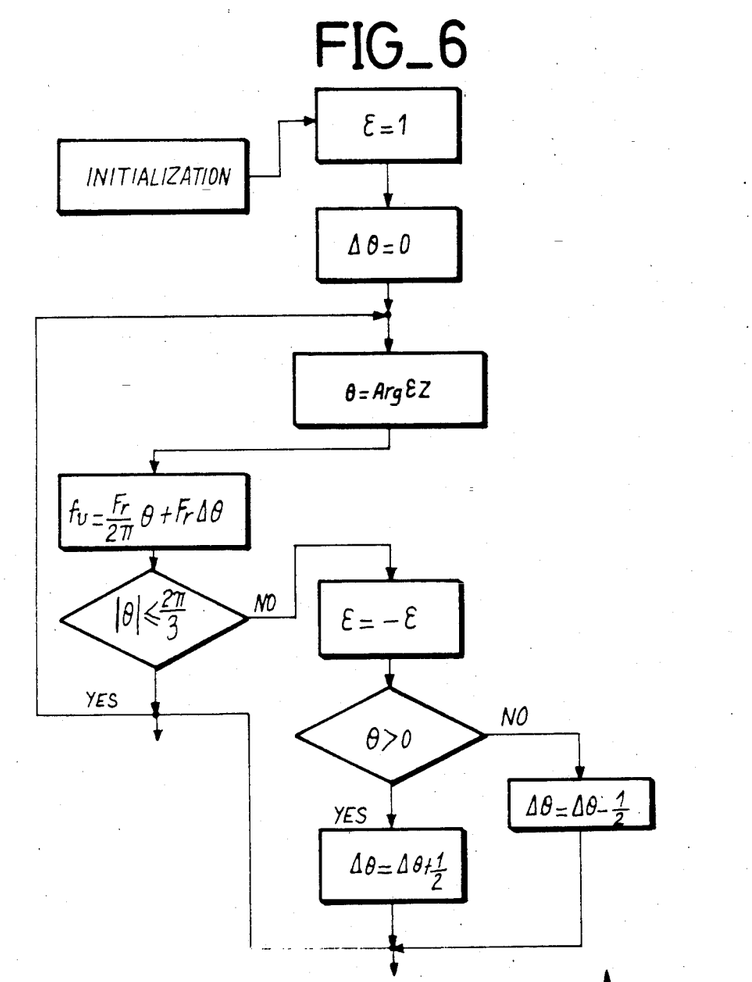
FIG. 6 an organigram showing the articulation of the different phases of the process according to the invention.

If $\Delta\theta$ designates the correction that must be applied to the full line graph that represents $Arg(\epsilon Z)$, to obtain the dashed line graph that represents the true value of the spaced to be measured it is possible to calculate $\Delta\theta$ according to an organigram represented in FIG. 6. The true Doppler shift will thus be expressed by:

$$f_v = \frac{F_r}{2\pi} \theta + F_r \cdot \Delta\theta$$

At the beginning of processing, at t shorter than t1, i.e. when it is certain that the Doppler shift measured is a true Doppler shift and not an ambiguous Doppler shift a true Doppler shift, $\epsilon$ is caused to be 1 and $\Delta\theta=0$. Then, $\theta = Arg(\epsilon Z)$ is calculated which means calculating the argument of Z since $\epsilon$ is equal to 1 (FIG. 6). This is again equivalent to taking for the correct result $f_m$, delivered by the analyser 10, i.e. without having modulated. Then, the true value $f_v$ is calculated acording to the preceding formula. Thereafter, the value of $\theta$ thus worked out is compared in absolute value to a value corresponding to the threshold. If the threshold is $F_r/3$ the absolute value of $\theta$ is compared to $2\pi/3$. If the absolute value of $\theta$ is lower than $2\pi/3$, neither $\epsilon$ nor $\Delta\theta$ are changed. At the following value delivered by analyser 10 this operation is repeated but by taking the algorithm downstream of the instructions that have imposed that $\epsilon$ be 1 and $\Delta\theta$ be 0.

By following the first segment of the full line graph, it will be noted that at an instant t1, $f_m$ become higher than $F_r/3$. The value of $f_v$ is nevertheless calculated as previously indicated. However, by comparing $\theta$ to $2\pi/3$ it is observed that $\theta$ is higher. The sign of $\epsilon$ is thus changed which in the present case becomes equal to $-1$ and a test is carried out on the sign of $\theta$. Here, $\theta$ is positive and $\Delta\theta$ is caused to be equal to $\Delta\theta + \frac{1}{2}$. At the value following that which was worked out at t1, it is calculated that $\theta = Arg \epsilon Z = Arg - Z$ which corresponds to the shifted value $f_d$. This means that a situation with modulation exists. Reference will now be made to the second segment of the full line graph of FIG. 5. The correction $\Delta\theta$ is no longer zero, but is equal to $\frac{1}{2}$ and is also accurately corrected from $+F_r/2$, the value called shifted value $f_d$ that is equal to $F_r \cdot \theta/2\pi$. At the instant t2, $Arg(\epsilon Z)$ is equal to zero and nothing happens for the correction $\Delta\theta$ nor for $\epsilon$ but simply $Arg(Z)$ changes value according to the convention mentioned herein-above. This has therefore no incidence upon the functioning of the algorithm of FIG. 6 since now $Arg(\epsilon Z)$ is calculated which passes it by zero.

At instant t3, the newly calculated $\theta$ becomes higher a second time than $2\pi/3$. In these conditions the sign of $\epsilon$ is again changed which now becomes $+1$. Since $\theta$ is still higher than zero (the full line graph at this instant is higher than zero) $\Delta\theta$ is caused to equal $\Delta\theta + \frac{1}{2}$ or $\Delta\theta = 1$. In other words, on the one hand there is no modulation but on the other hand the calculated $\Delta\theta$ corresponds to having shifted twice in the same direction; the correction takes into account the two successive shifts. At the instant t4 there is even a third shift which means that $\Delta\theta$ becomes equal to 3/2. On the contrary, at the instant t5, $\theta$ which is negative, becomes higher in absolute value than the value $2\pi/3$. The same operations as before are carried out on $\epsilon$ but it is interesting to note that in this case $\Delta\theta$ is caused to equal $\Delta\theta - \frac{1}{2}$ since now $\theta$ is negative. Consequently, once the correction has been made, that which was previously 3/2; is now only equal to 1. The correction evolves cumulatively and so on through addition or subtraction, wherever necessary.

Figure 8:
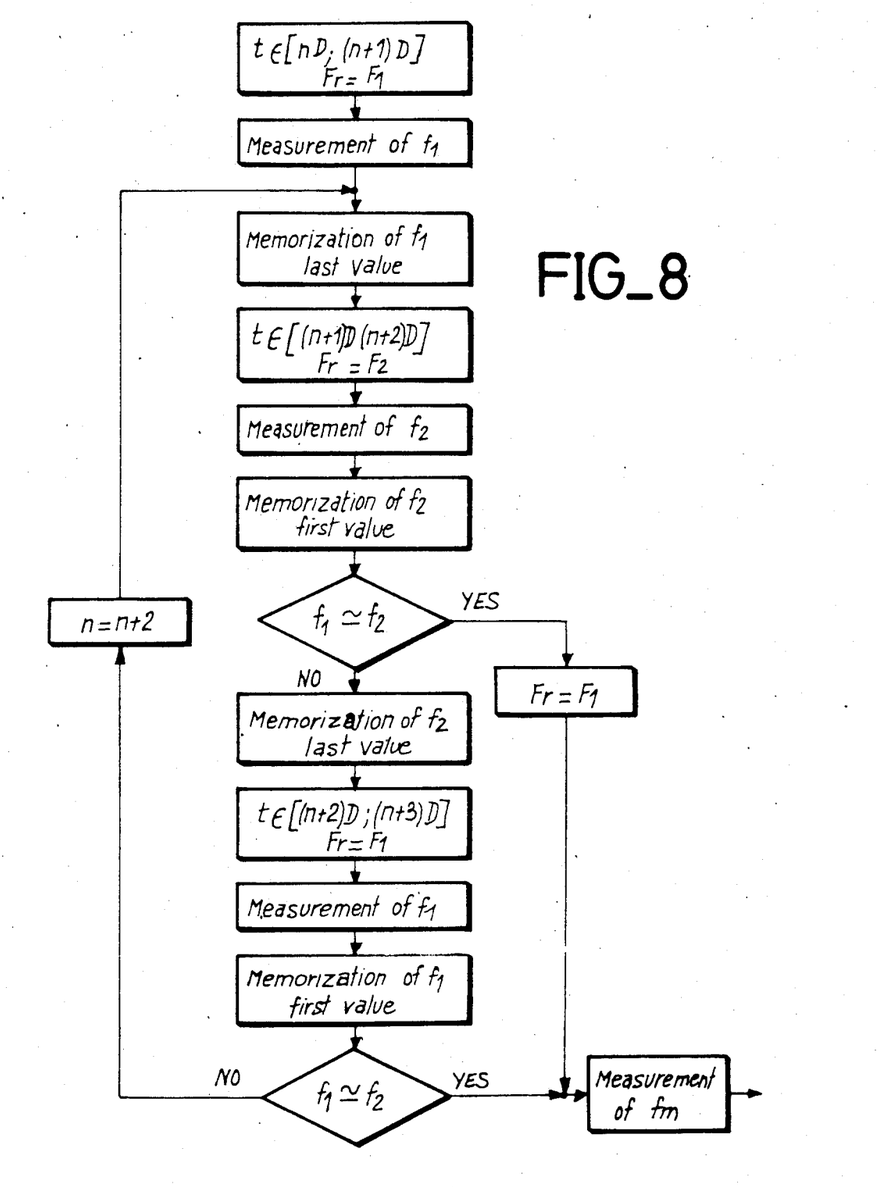
FIG. 8 an organigram allowing the initiation of the process according to the invention.

It was stated herein-above that operating begins from a situation where it was certain that the measurement of the speed was not an ambiguous measurement but was a true measurement. Then, when the experimentation begins, it is not exactly certain that this situation is prevailing. Consequently, it may be useful to carry out an initialization step prior to the beginning of the process according to the invention for finally removing all ambiguity from a measurement. In this way, the certainty is acquired that measurements of true speeds are being made and not ambiguous speeds of true speeds. This initialization phase will be now described with reference to FIG. 8 which represents its organigram.

The principle that is used in this initialization consists in choosing successive time intervals during which the recurrence frequency assumes different values. Then, in comparing the result obtained on the measurement of speed at the end of an interval with the result obtained at the beginning of the following interval it is possible to state when these results are substantially the same, that the speed measured in one case as in the other and when there has not been sufficient time for the speed to change from the end of one interval to the beginning of the following, is a true speed. Indeed, it appears that if the measurements carried out were ambiguous measurements of true speeds, from the fact that the recurrence frequencies are different, they must be different from one case to another. In one example two frequencies $F_1$ and $F_2$ are retained which impose the rhythm of the pulses alternately in one time interval and in the following one. It should be noted, however, that this recurrence frequency change does not modify the functioning of analyser 10 (already described) since it is controlled by a sequencer 27 that is exactly synchronized on the recurrence period itself.

In the medical field where measurements of the speed of blood are taken, the different analysis intervals, with one or other frequency, will be dependent upon the patient's cardiac rhythm. By considering, for example, a minimal duration of cardiac beats equal to 0.3 second (which is equivalent to a cardiac rhythm of about 200 beats per minute and which seems from this point of view to be a limit value), the following consideration is reached; it is necessary to be able to verify the equality of speeds during a single cardiac cycle and not from one cardiac cycle to another. Consequently, successive intervals of 0.1 second (10 Hz) allow to affirm that there are very high chances that, during the passage from one interval to another, the speed variation of the blood is relatively low. With a recurrence frequency equal alternately to 6 KHz and 8 KHz it is possible to acquire during each interval of 0.1 second respectively 600 to 800 samples.

Since about a hundred samples are required in order to work out a measurement of the mean Doppler shift, but since these measurements are however given in real time by analyser 10 at the rhythm of the sampling, it is necessary to compare the last value acquired during a given interval with the first value acquire in the following for which the whole of the samples is only intrinsically dependant upon the new retained recurrence frequency. In practice, it is necessary to await receiving the $P^{th}$ sample in the fresh interval in order to work out the "first" mean Doppler shift value that corresponds to this interval.

It is not necessary that the intervals concerned be periodically distributed during time. The dates which separate the different intervals can be chosen at random. It is even eventually possible to determine these dates of recurrence frequency change once the mean Doppler shift $f_m$ reaches and exceeds a certain threshold. However, the organigram of FIG. 7 corresponds to intervals of duration D, all of which are equal. Therefore, during a first interval when the measurement date t is comprised between nD and (n+1)D, it is necessary that the recurrence frequency $F_r$ be equal to $F_1$. The mean Doppler shifts are measured during this time: their value is $f_1$. At the end of this duration the last value of $f_1$ is memorized. For the following duration, for dates comprised between (n+1)D and (n+2)D, it is necessary that the recurrence frequency be equal to $F_2$. The mean Doppler shift obtained is thus measured according to this new recurrence frequency, their value being $f_2$. The first value of $f_2$ is memorized that is completely disconnected from measurement of $f_1$ (i.e. P sample later). Once $f_2$ is acquired, $f_2$ is compared to $f_1$. If these two values are equal, it can be deduced that both are true values and therefore an initialized situation exists. In these conditions, it is necessary that the recurrence frequency assumes one of two values that have been chosen for the initialization: for example $F_1$. At this moment, the calculation process described by the algorithm of FIG. 6 begins, during which all ambiguities will be removed that could be present on the speed measurement of the target progressively as they arise.

On the other hand, if $f_1$ is different from $f_2$, this means that at least one of these measurements is ambiguous. In these conditions it is not yet possible to take a decision since it is not known which of these two measurements is a true measurement and even if one of them is a true measurement. Consequently, the whole of the initialization operations carried out up till now are repeated but this time by memorizing the last measured value of $f_2$. During the following interval, after having changed the recurrence frequency from $F_2$ to $F_1$, the "first" value of $f_1$ is measured and memorized. Then the last memorized values of $f_1$ and $f_2$ are again compared. If they are equal, it is possible to affirm that initialization has been carried out; if they are not equal the whole of the operation is repeated until the initialization is obtained.

The following comments can be made which are advantageous in the case of medical application of the invention. By observing a time diagram of the circulation speeds of blood, it is perceived that statistically these circulation speeds are more often low than high. The chances of finding low speeds, thus true speeds, are thus high. This is the reason why the initialization process immediately described hereinabove operates well. This would not necessarily be the case of a phenomenon where the displacement speeds would be high and would statistically often provoke ambiguous measurements of the true speeds. In these latter conditions the intialization phase will last longer but will even so finish by obtaining at a given moment a true value. The process described in FIG. 7 allows to obtain the true value with certainty, over approximately two successively cardiac cycles, which is overall very satisfactory.

It must however be acknowledged that this initialization can be rendered incorrect. Indeed, it can happen that $f_1$ is equal to $f_2$ while each of these measurements is an ambiguous measurement of a true speed. This means that the true speed will thus correspond to the smallest common multiple of the two recurrence frequencies retained. The example given would then feature a Doppler shift higher than 24 KHz. A simple method to repel as high as possible this ambiguity threshold for which the initialization is incorrect consists in choosing frequencies $F_1$ and $F_2$ that are first numbers between them, for example, 7 KHz and 8 KHz. This will bring the ambiguity in Doppler shift to 56 KHz which for retained sonic or acoustical frequencies in the present description would correspond to circulation speeds of blood of about 20 m per second and which would be truly exceptional. It is, however, necessary that each of frequencies $F_1$ and $F_2$ be an exact sub-multiple of sonic or acoustical frequency $f_o$.

The initialization phase can, however, be suppressed. In particular, in a medical application, it is noted that during a cardiac cycle, the instantaneous speed is low throughout relatively long durations at the end of this cardiac cycle. At low speed the signal/noise ratio of S(t) is worse due to the presence of steady echo filters. These filters tend to eliminate in S(t) the spectral contribution due, for example, to the capillary walls. Consequently, during a cardiac cycle when the energy of the useful Doppler signal becomes weak during relatively long periods, low speeds which are not ambiguous are present. In order to suppress the initialization the ambiguity correction algorithm is thus synchronized over such a period.

I claim:

1. Process for removing all ambiguity from the measurement by Doppler effect of the speed of a target comprising the steps in which a pulse vibrating at a sonic or acoustical frequency is emitted in the direction of a target, periodically at a recurrence frequency;

the ultrasonic pulse retrodiffused by the target is received;

a complex demodulation of the signal received is carried out, by a signal of the same frequency as the emitting sonic or acoustical frequency;

the speed of the target is calculated by spectral analysis from the Doppler shift signal resulting from the demodulation, this shift being representative of the speed of the target, the determination ambiguity of the speed of the target being induced by the importance of this shift with respect to the half recurrence frequency, wherein the speed calculated by spectral analysis is compared to a threshold, and when it overruns this threshold, said demodulated signal is modulated by a signal oscillating at a determination frequency so as to transpose, by a known value, the Doppler shift to be measured in a band smaller than the half of the recurrence frequency and;

wherein the calculation of the speed of the target comprises calculating by spectral analysis a shifted speed from this modulated signal and correcting said shifted speed by a width corresponding to the determination frequency in order to elaborate the true speed to be measured; and optionally performing one or more supplemental modulations and a corresponding corrections when the so shifted speeds overrun another threshold.

2. Process according to claim 1, wherein the determination frequency is equal to half the recurrence frequency.

3. Process according to claim 1, wherein the modulation consists in multiplying the demodulated signal by a signal oscillating at the determination frequency.

4. Process according to claim 1, wherein the spectral analysis comprises elaboration of the self-correlation function of the modulated signal and calculation of the order one derivate of this function to deliver a result that is representative of the mean shifted speed of the target.

5. Process according to claim 3, wherein the spectral analysis comprises the elaboration of the self-correlation function of the demodulated signal and the calculation of order one derivate of this function to deliver a result that is representative of the ambiguous mean speed of the target and wherein the modulation of the demodulated signal is replaced by a modification brought to this result in the form of a shift constant that replaces the modulation.

6. Process according to claim 1, wherein the correction is brought to the shifted speed in the cumulative form of additive or subtractive constants, calculated in advance, and the values of which depend upon the ratio connecting the determination frequency to the recurrence frequency, these corrections being additive when the transposed Doppler shift is positive and being negative when this transposed Doppler shift is negative.

7. Process according to claim 1, wherein it is preceded by an initialization step in which the recurrence frequency assumes different values during successive time intervals and wherein the last speed measurement worked out at the end of an interval is compared to the first speed measurement worked out at the beginning of the following interval to determine that none of these measurements is ambiguous when they are substantially equal to one another.

8. Process according to claim 1, wherein the shifted mean speed is measured either on the one hand without modulating the demodulated signal when the speed measured is lower than a given threshold ($F_r/3$) given being itself lower than a speed called nominal speed that corresponds to the half recurrence frequency, or on the other hand, by modulating the demodulated signal when the speed becomes higher than this threshold.

9. Process according to claim 8, wherein the given threshold corresponds to ⅜ of the recurrence frequency.

10. Process according to claim 8, wherein the correction is cumulatively elaborated in function of the directions of the evolutions of the shifted speed around the threshold speed.

11. Process according to claim 7, wherein the time intervals are of any given duration.

12. Process according to claim 7, wherein the time intervals are equal between one another.

13. Process according to claim 7, wherein the time intervals are determined by dates which mark the passage of the measurements of shifted speed at predetermined values.

* * * * *